United States Patent [19]

Ishikawa et al.

[11] 4,011,250
[45] Mar. 8, 1977

[54] 1α, 2α-DIHYDROXYCHOLECALCIFEROL AND PROCESS FOR PREPARING THE SAME

[75] Inventors: Masayuki Ishikawa; Chikara Kaneko, both of Tokyo; Satoshi Sasaki, Higashiyamato; Tatsuo Suda, Tachikawa; Sachiko Yamada, Kawagoe; Akiko Sugimoto, Hino, all of Japan

[73] Assignees: Masayuki Ishikawa; Chikara Kaneko; Satoshi Sasaki; Tatsuo Suda, all of Tokyo, Japan

[22] Filed: Aug. 6, 1975

[21] Appl. No.: 602,363

[30] Foreign Application Priority Data

Aug. 7, 1974 Japan .................... 49-89835

[52] U.S. Cl. .................... 260/397.2; 260/239.5
[51] Int. Cl.² .................... C07J 71/00; C07J 9/00

[58] Field of Search ....... 260/617 D, 617 A, 397.2, 260/631 R, 617 R

[56] References Cited
OTHER PUBLICATIONS

Kaneko et al., Steroids, vol. 23(1), pp. 75–92 (1974).
Pelc, J. Chem. Soc., Perkin I, pp. 1436–1438 (1974).
Boomsma et al., Tetrahedran Letters, pp. 427–430 (1975).

*Primary Examiner*—Elbert L. Roberts
*Attorney, Agent, or Firm*—Browdy and Neimark

[57] ABSTRACT

1α,2α-Dihydroxycholeciferol having improved vitamin D activities and a process for preparing the same are disclosed.

1 Claim, 1 Drawing Figure

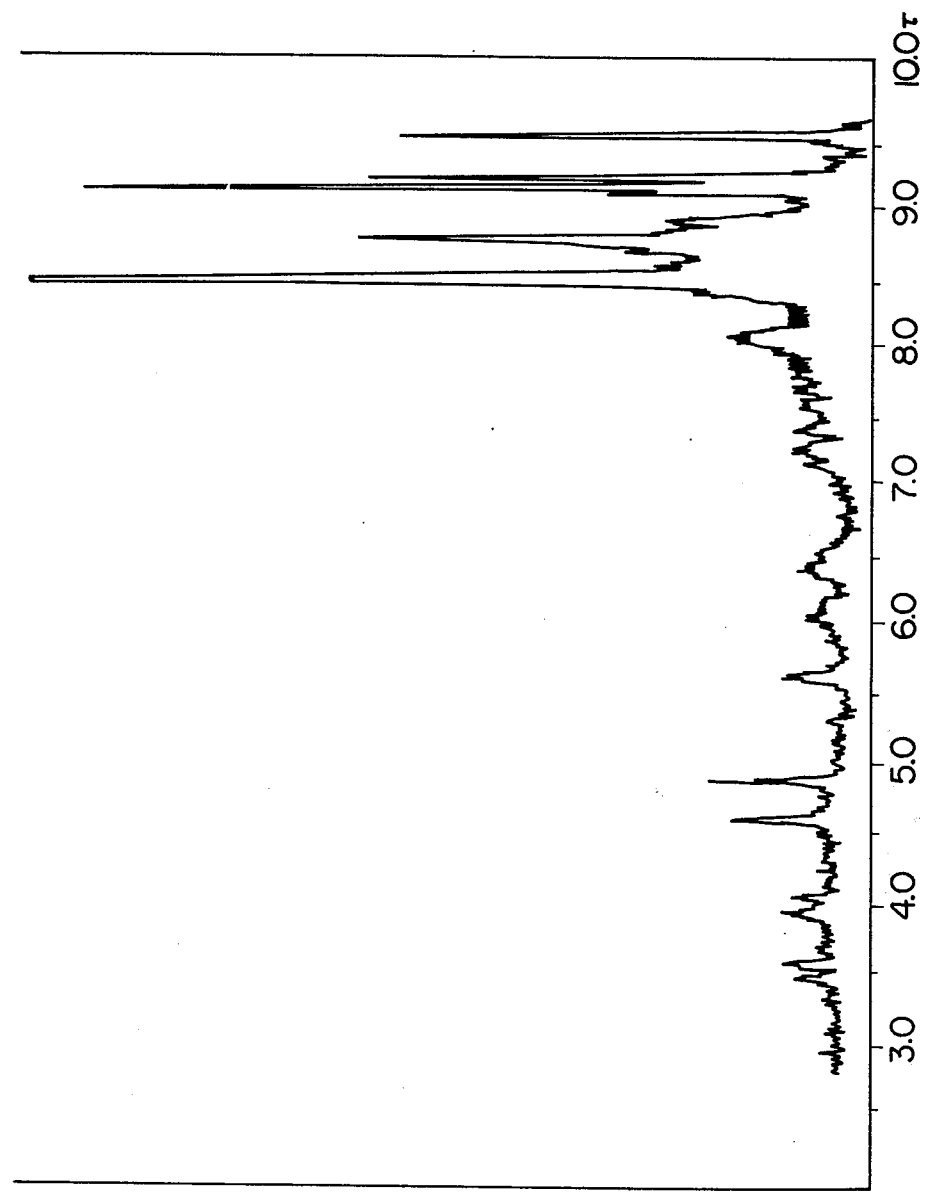

1α, 2α-DIHYDROXYCHOLECALCIFEROL AND PROCESS FOR PREPARING THE SAME

This invention relates to a novel compound, 1α, 2α-dihydroxycholecalciferol and a process for preparing the same.

The object compound of this invention is useful as vitamin D.

According to this invention, 1α,2α-dihydroxycholecalciferol is prepared by irradiating the compound represented by the formula (IV)

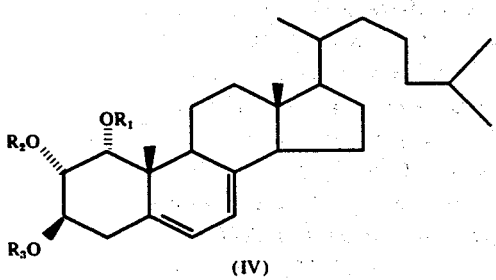

wherein $R_1$, $R_2$ and $R_3$ are identical or different and are hydrogen or acyl, with ultraviolet light to form a previtamin $D_3$ derivative represented by the formula (III)

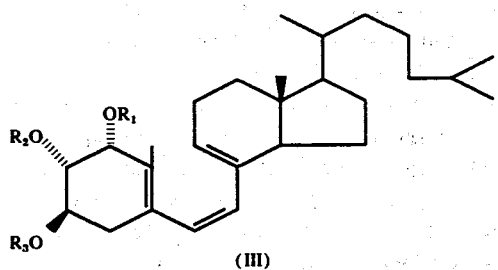

wherein $R_1$, $R_2$ and $R_3$ are as defined above and isomerizing the derivative to obtain the vitamin $D_3$ derivative represented by the formula (II)

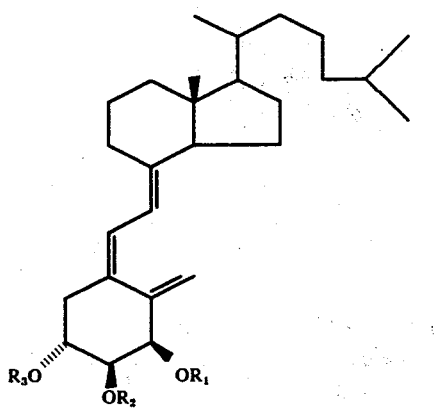

wherein $R_1$, $R_2$ and $R_3$ are the same as defined above, and deacylating the previtamin $D_3$ when at least one of $R_1$, $R_2$ and $R_3$ is acyl.

In the practice of this invention, the photoreaction caused by the radiation of ultraviolet light may be preferably carried out in a solvent, for example, hydrocarbons, ethers and alcohols. In particular, the hydrocarbons are, for example, saturated hydrocarbons, preferably, those having a low boiling point such as hexane, octane and the like. As esters, saturated ethers are preferable, and saturated ethers having a low boiling point, particularly, diethyl ether, tetrahydrofuran and the like are preferred. Alcohols which are useful in this invention are lower alcohol, more particularly methanol. The photoreaction may be conveniently carried out at a temperature below 35° C in an atmosphere of an inert gas such as argon or the like. The radiation time of ultraviolet light varies depending upon the ultraviolet light source and the scale of the reaction system to be carried out; it may be several tens of seconds to several hours.

This ultraviolet light radiation produces previtamin $D_3$ derivative represented by the formula (III) which is derived from the compound represented by the formula (IV) by B-ring cleavage of its steroid skeleton.

The vitamin $D_3$ derivative (II) is then prepared by isomerizing the previtamin $D_3$ derivative (III). The isomerization is carried out by allowing the previtamin derivative to stand in a suitable solvent in a dark place or by heating the derivative in a solvent. The solvent to be used may be any solvent which is inert when the reaction is carried out and, usually, aliphatic hydrocarbons, ethers, alcohols and benzene and its derivatives may be used. It is perferable to use a solvent having a low boiling point and excellent power to dissolve the previtamin $D_3$ derivative (III), particularly hexane, octane, toluene, diethyl ether, tetrahydrofuran and the like. The reaction time varies within the range of from several hours to several weeks depending upon reaction conditions used. When the previtamin is kept at a temperature below 35° C in a solvent in a dark place, a reaction time of several weeks in preferable. However, when the reaction is carried out under reflux, a reaction time of several hours is preferable. It is also preferable to carry out the isomerization in an atmosphere of an inert gas such as nitrogen, argon or the like.

The object compound of this invention is 1α,2α-dihydroxycholecalciferol (I) which may be represented by the formula (II) wherein each of $R_1$, $R_2$ and $R_3$ is hydrogen. However, the compound represented by the formula (II) wherein at least one of $R_1$, $R_2$ and $R_3$ is an acyl may be deacylated to produce the object compound (I).

In the deacylation step, a deacylating agent, usually a basic substance or a metal hydride is used. The basic substance is, for example, an alkali metal hydroxide, particularly, sodium hydroxide, potassium hydroxide or the like. For the metal hydride, aluminum lithium hydride, boron lithium hydride, boron sodium hydride or the like is usually used. The solvent to be used in the deacylation step is selected, depending upon the type of deacylating agent. When an alkali metal hydroxide is used as deacylating agent, it is suitable to use water, an alcohol or a mixture of water and an organic solvent, particularly water, methanol or ethanol or a mixture of water and diethyl ether. In case the deacylation is effected by reduction with the use of a metal hydride, the preferred solvent is an ether, for example, diethyl ether, tetrahydrofuran, 1,2-dimethoxyethane, diethylene glycol dimethyl ether and the like. However, if boron sodium hydride is used, a compound having at least one hydroxy group, such as water, methanol, ethanol and the like may be used as solvent.

The reaction temperature may vary within the range of from 20° C to reflux temperature of the solvent used, depending upon the type of deacylating agent. When an alkali metal hydroxide is used as the deacylating agent, a temperature lower than 100° C is preferable. In contrast, the deacylating reaction may be carried out at a temperature in the broad range of from 20° C to reflux temperature of the solvent used, when a metal hydride is used as deacylating agent.

In accordance with this invention, the object compound and an intermediate produced in each step of the process of this invention may be isolated or purified by a conventional method, for example, extraction, recrystallization, column chromatography, partition chromatography and the like, and particularly, column chromatography with Sephadex (manufactured by Pharmacia Fine Chemicals Co.) being suitable. However, the isolation of the intermediate is not essential in this invention, and therefore, the process of this invention can proceed through the above mentioned route without isolation of an intermediate.

The thus obtained $1\alpha,2\alpha$-dihydroxycholecalciferol clearly exhibits vitamin D activities even by daily oral administration. The activities were confirmed by using young rats which had been bred for two weeks with food low in calcium and vitamin D. In this method, intestinal calcium transport activity and bone calcium mobilization activity were determined by measuring the change of serum calcium.

The starting compound of this invention represented by the formula (IV) is usually derived from a steroid compound. For example, hydroxy radicals and double bonds should be introduced into cholesterol in order to obtain the compound (IV). In this reaction, a hydroxy radical which is originally present in cholesterol should be protected depending on specific conditions used. This fact will become clear by the description herein below. The starting compound represented by the formula wherein $R_1$, $R_2$ and $R_3$ are a hydrogen atom is one which the protective radicals have been removed prior to the process of this invention, or one which has been prepared without introducing any protective radical. Although there is no essential difference in the progress of both the reaction with irradiation of ultraviolet light and the isomerization reaction between the starting compound having protective groups and the compound having no such group, the solubility of the compound in a solvent used can be improved by selecting specific radicals for $R_1$, $R_2$ and $R_3$ to effect the reaction smoothly.

The protective group used in this invention is usually an acyl radical, which includes aliphatic acyl radicals and aromatic acyl radicals. The aliphatic acyl radicals include, for example, saturated aliphatic acyl radicals, more particularly aliphatic lower acyl radicals and preferably saturated aliphatic acyl radicals having 1-4 carbon atoms. The specific acyl radicals are acetyl, propionyl and butyryl. Suitable aromatic acyl radicals are for example mononucleus aromatic acyl radicals, particularly benzoyl radical.

The starting compounds (IV) which are novel include, for example, $1\alpha,2\alpha,3\beta$-triacetoxy-cholesta-5,7-diene, $1\alpha,2\alpha,3\beta$-tribenzoxy-cholesta-5,7-diene, $1\alpha,2\alpha$-dipropionyloxy-3$\beta$-acetoxy-cholesta-5.7-diene, $1\alpha,2\alpha$-diacetoxy-3$\beta$-benzoxycholesta-5,7-diene, $1\alpha,2\alpha$-dibenzoxy-3$\beta$-acetoxy-cholesta-5,7-diene and $1\alpha,2\alpha,3\beta$-trihydroxy-cholesta-5,7-diene.

The starting compounds enumerated above may be prepared by, for example, a process disclosing hereinbelow. The process comprises acylating 3$\beta$-hydroxy-cholesta-1,5-diene (V) to obtain 3$\beta$-acyloxy-cholesta-1,5-diene (VI), reacting the compound (VI) with osmium tetraoxide to give $1\alpha,2\alpha$-dihydroxy-3$\alpha$-acyloxy-cholesta-5-ene (VII), diacylating the compound (VII), halogenating the corresponding $1\alpha,2\alpha$-diacyloxy compound (VIII) and dehydrohalogenating the resulting $1\alpha,2\alpha,3\beta$-triacyloxy-7-halogen-cholesta-5-ene (IX). Among the compounds (IV), the compound of the formula wherein $R_1$, $R_2$ and $R_3$ is hydrogen i.e. $1\alpha,2\alpha,3\beta$-trihydroxy-cholesta-5,7-diene may be prepared by, for example, hydrolizing the corresponding $1\alpha,2\alpha,3\beta$-triacyloxy compound with the use of an alkali metal hydroxide such as sodium hydroxide potassium hydroxide or the like, or by reductively deacylating the compound with the use of a metal hydride such as boron sodium hydride, aluminium lithium hydride or the like.

Alternatively, in order to prepare $1\alpha,2\alpha,3\beta$-trihydroxy compound from the corresponding $1\alpha,2\alpha,3\beta$-triacyl compound in a high yield, a triazoline-3,5-dione derivative, for example, 4-phenyl-1,2,4-triazoline-3,5-dione, 4-methyl-1,2,4-triazoline-3,5-dione, 4-methyl-1,2,4-triazoline-3,5-dione or the like is added to a mixture containing the $1\alpha,2\alpha,3\beta$-triacyloxy compound to give 1,4-addition product represented by the formula (X)

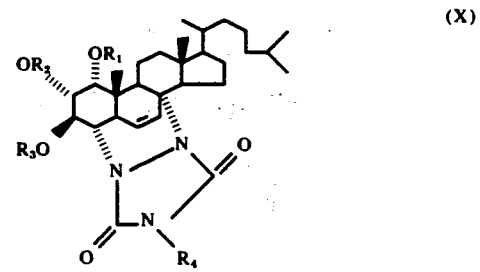

wherein $R_1$, $R_2$ and $R_3$ are independently an acyl and $R_4$ is an aryl or alkyl. After isolation of the addition product (X), it is subjected to reductive deacylation by the use of a metal hydride, for example, aluminium lithium hydride to obtain the object compound.

This alternative process can be illustrated by the following reaction scheme. In the formula in the scheme, Ac and Ac' are identical or different and are an acyl, X is a halogen atom and R is an aryl or alkyl.

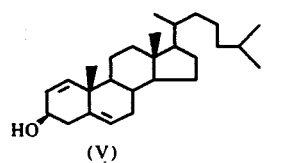
(V)

↓ acylation

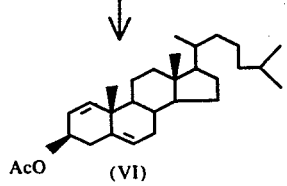
(VI)

↓ OsO₄

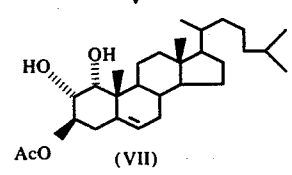
(VII)

↓ acylation

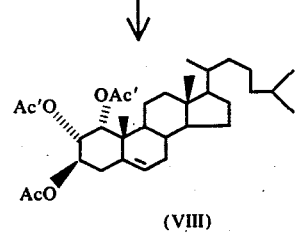
(VIII)

↓ halogenation

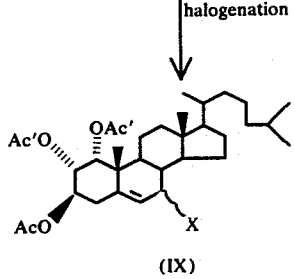
(IX)

↓ dehydrohalogenation

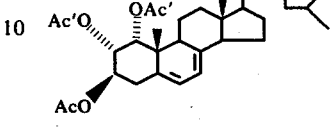
(IVa)

↓ hydrolysis (IVb)    (X)

reduction

This invention will be explained in detail by the following Examples.

EXAMPLE 1

A solution of 1α,2α,3β-trihydroxy-cholesta-5,7-diene (21.2 mg) in dried diethylether (600 ml) was irradiated with light from 200 W high pressure mercury lamp in an argon stream for 8 minutes, and just after the completion of the irradiation, the solvent used was removed. The residue was subjected to column chromatography with the use of Sephadex LH-20 column (manufactured by Pharmacia Fine Chemicals Co., being identical hereinbelow) and a solvent (chloroform : hexane = 8 : 2) to obtain 1α,2α-dihydroxyprevitamin $D_3$ (6.66 mg). The resulting previtamin $D_3$ derivative was dissolved in diethyl ether (20 ml) and placed in a vessel having a stopper. After the purge of air in the vessel by argon, the vessel was stoppered and allowed to stand in a dark place at room temperature for 10 days and then the solution was subjected to column chromatography with the use of Sephadex LH-20 and a solvent (chloroform : hexane = 8 : 2) to obtain 1α,2α- dihydroxy cholecalciferol (3.37 mg). The NMR spectrum of the product is shown in the attached drawing.
Mass spectrum m/e: 416 (M+), 398, 380, 362, 249
U.V. spectrum $\lambda_{max}^{Et2O}(\epsilon)$: 267 nm (18,000)

EXAMPLE 2

A solution of 1α,2α,3β-triacetoxy-cholesta-5,7-diene (50 mg) in dried diethyl ether (600 ml) was irradiated with light from 200 W high pressure mercury lamp in an argon stream for 12 minutes and, just after the completion of the irradiation, the solvent used was distilled off under reduced pressure. The residue was then subjected to column chromatography with Sephadex LH-20 column and a solvent (chloroform : hexane = 65 : 35) to obtain 1α,2α-diacetoxy-previtamin $D_3$-acetate (20 mg). The resulting previtamin $D_3$ derivative was dissolved in diethyl ether (30 ml) and the solution was placed in a vessel which was purged with argon and sealed. After keeping the vessel in a dark place for 10 days, the solution was subjected to a column chromatography with Sephadex LH-20 column and a solvent (chloroform : hexane = 65 : 35) to obtain 1α,2α-diacetoxy-vitamin $D_3$-acetate (7 mg). The acetate was dissolved in a amount of diethyl ether and to the solution was added a mixture of 10% potassium hydroxide aqueous solution (10 ml) and methanol (20 ml) followed by heating the resulting mixture at a temperature of from 40° to 50° C in an argon stream for 5 hours. After methanol was distilled off, the mixture was extracted with diethyl ether and the extract was dried over magnesium sulfate and concentrated under reduced pressure. The residue was subjected to column chromatography with the use of Sephadex LH-20 column and a solvent (chloroform : hexane = 65 : 35) to obtain 1α,2α-dihydroxycholecalciferol (4 mg). The product obtained was assayed and it was confirmed that mass spectrum, U.V. spectrum and NMR spectrum of the product are identical to those of the product obtained in Example 1.

The preparation of the starting compound is illustrated by the following Example 3.

EXAMPLE 3

Preparation of the starting compound

3β-Hydroxy-cholesta-1,5-diene (500 mg) was dissolved in acetic anhydride containing several drops of pyridine (20 ml). After heating the solution for 2 hours on a hot water bath, the solution was poured into ice-water, extracted with ether, washed with an alkali and concentrated. The residue was recrystallized from methanol to obtain 3β-acetoxy-cholesta-1,5-diene having a melting point between 73 and 75° C.

3β-Acetoxy-cholesta-1,5-diene (1.6 g) was dissolved in diethyl ether (50 ml) and to the solution were added osmium tetraoxide (1 g) and pyridine (500 mg). After the mixture was stirred at room temperature for 5 days, pyridine (20 ml) and 10% sodium bisulfite aqueous solution (50 ml) were added and the mixture was further stirred at room temperature overnight. The mixture was extracted with 100 ml of ethyl acetate, and then the remaining aqueous phase was extracted twice with ethyl acetate, and the obtained extracts were combined. The combined extract was washed twice with water, dried over magnesium sulfate and subjected to distillation to remove the solvent used. The residue was dissolved in chloroform and subjected to column chromatography with alumina column to obtain 1α,2α-dihydroxy-3β-acetoxy-cholesta-5-ene having a melting point between 131 and 133° C.

1α,2α-Dihydroxy-3β-acetoxy-cholesta-5-ene (264 mg) was dissolved in a mixture of acetic anhydride (20 ml) and pyridine (2 ml) and the solution was heated on a boiling water bath for 2 hours to remove acetic anhydride. To the solution was added ice-water and the precipitated crystals were recovered by filtration. Recrystallization of the crystals from methanol yielded 1α,2α,3β-triacetoxycholesta-5-ene (230 mg) having a melting point between 109 and 110° C.

1α,2α,3β-Triacetoxy-cholesta-5-ene (300 mg) was dissolved in a mixture of petroleum benzine (5 ml) and benzene (5 ml). To the solution was added 1,3-dibromo-5,5-dimethyl hydantoin (95 mg) and the resulting solution was heated on water bath at 70° C for 20 minutes. After cooling the solution, precipitated crystals was filtrated off and the filtrate was concentrated under reduced pressure to dryness. The resulting bromide (3 ml) as crude product was dissolved in xylene. A mixture of trimethyl phosphite (1 ml) and xylene (3 ml) was added dropwise to the solution while refluxing it mildly in an argon stream. After continuously refluxing for 2 hours, the solvent was distilled off. The resulting 1α,2α,3β-triacetoxy-cholesta-5,7-diene was dissolved in diethyl ether (10 ml) and to the solution was added slowly 4-phenyl-1,2,4-triazoline-3,5-dione. About 25 mg of triazoline was required. After continuously stirring the mixture for 1 hour, diethyl ether was distilled off and then the residue was subjected to column chromatography with the use of alumina column and a solvent (diethyl ether : hexane = 1 : 1) to obtain 1,4-addition product of 1α,2α,3β-triacetoxy-cholesta-5,7-diene as oil represented by the formula

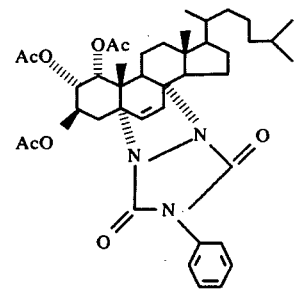

wherein Ac is an acetyl.

NMR spectrum (CDCl$_3$); 2.5–2.8 (5H, multiplet, hydrogen atoms of phenyl radical) 3.7 (2H, AB quartet, hydrogen atoms of C$_6$ and C$_7$ position)

The thus obtained 1,4-addition product (108 mg) was dissolved in tetrahydrofuran (10 ml) and the solution was added dropwise to a solution of aluminium lithium hydride (100 mg) in tetrahydrofuran (20 ml) while stirring. After cooling the solution, the remaining aluminium lithium hydride was decomposed by wet sodium sulfate and ethyl acetate (about 100 ml) was added to the solution. After drying it over magnesium sulfate, the solvent was distilled off. The residue was subjected to column chromatography with silica gel column and eluted with chloroform-methanol (100 : 1). The elute was concentrated and recrystallized from methanol to obtain 1α,2α,3β-trihydroxy-cholesta-5,7-diene having a melting point between 154°– 156° C.

Mass spectrum m/e; 416 (m$^+$398, 380, 354

What is claimed is:

1. 1α,2α-dihydroxycholecalciferol represented by the formula

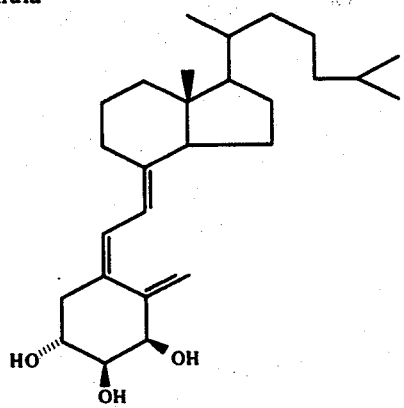

* * * * *

UNITED STATES PATENT AND TRADEMARK OFFICE
CERTIFICATE OF CORRECTION

PATENT NO. : 4,011,250
DATED : March 8, 1977
INVENTOR(S) : ISHIKAWA et al

It is certified that error appears in the above-identified patent and that said Letters Patent are hereby corrected as shown below:

Column 4, line 13, that portion of the formula reading $-3\alpha-$ should read $-3\beta-$ Column 9, line 18, $(m^+ 398,$ should read $(M^+)$ 398, Signed and Sealed this second Day of August 1977

[SEAL]

Attest:

RUTH C. MASON
Attesting Officer

C. MARSHALL DANN
Commissioner of Patents and Trademarks